United States Patent
Carter et al.

(10) Patent No.: US 10,308,571 B2
(45) Date of Patent: Jun. 4, 2019

(54) PROCESS FOR MINIMIZING BENZENE, TOLUENE, AND A RECYCLE LOOP IN A ZERO BENZENE AROMATICS COMPLEX

(71) Applicant: UOP LLC, Des Plaines, IL (US)

(72) Inventors: Elizabeth A. Carter, Arlington Heights, IL (US); Deng-Yang Jan, Elk Grove Village, IL (US); Timur V. Voskoboynikov, Arlington Heights, IL (US)

(73) Assignee: UOP LLC, Des Plaines ( * ) Notice: Subject to any disclaimer, the term of this patent is extended or adjusted under 35 U.S.C. 154(b) by 0 days.

(21) Appl. No.: 15/730,532

(22) Filed: Oct. 11, 2017

(65) Prior Publication Data

US 2019/0106368 A1    Apr. 11, 2019

(51) Int. Cl.
  *C07C 2/66* (2006.01)
  *C07C 6/06* (2006.01)

(52) U.S. Cl.
  CPC .......... *C07C 6/06* (2013.01); *C07C 2/66* (2013.01); *C07C 2521/04* (2013.01); *C07C 2529/06* (2013.01)

(58) Field of Classification Search
  CPC ......... C07C 6/06; C07C 2/66; C07C 2521/04; C07C 2529/06; C07C 2/76–868; C07C 5/27
  See application file for complete search history.

(56) References Cited

U.S. PATENT DOCUMENTS

| | | | |
|---|---|---|---|
| 5,866,740 A | 2/1999 | Mikitenko et al. | |
| 7,304,193 B1 | 12/2007 | Frey et al. | |
| 9,249,068 B2 | 2/2016 | Tinger et al. | |
| 2012/0149958 A1* | 6/2012 | Ellrich | C07C 2/864 585/321 |
| 2013/0267746 A1* | 10/2013 | Ding | C07C 6/06 585/319 |
| 2014/0100398 A1* | 4/2014 | Jin | C07C 2/76 585/254 |
| 2016/0264495 A1* | 9/2016 | Molinier | B01D 3/141 |
| 2017/0073285 A1* | 3/2017 | Whitchurch | C07C 2/64 |

FOREIGN PATENT DOCUMENTS

| | | |
|---|---|---|
| IN | 201617037477 A | 2/2017 |
| KR | 473672 B1 | 7/2005 |
| WO | 2013151710 A1 | 10/2013 |

(Continued)

OTHER PUBLICATIONS

Otani, Process Flowsheet/Benzene, Xylene Bonanza From Less-Prized Aromatics, Chem Eng V77 N. 16 118-20 (Jul. 27, 1970), Jul. 27, 1970.

(Continued)

*Primary Examiner* — In Suk C Bullock
*Assistant Examiner* — Ali Z Fadhel

(57) ABSTRACT

The present invention relates to minimizing benzene, toluene, and an A9/A10 recycle loop in a zero benzene aromatics complex. More specifically, the present invention relates to a minimizing benzene, toluene, and an A9/A10 recycle loop in a zero benzene aromatics complex wherein the aromatic feed has a low methyl to phenyl ratio, and where the aromatic feed has a high methyl to phenyl ratio.

18 Claims, 3 Drawing Sheets

(56) References Cited

FOREIGN PATENT DOCUMENTS

| WO | 2015017103 A1 | 7/2014 |
| WO | 2017044137 A1 | 3/2017 |
| WO | 2017105848 A1 | 6/2017 |

OTHER PUBLICATIONS

Grandio et.al., Toluene for Benzene and Xylenes, Hydrocarbon Processing, v 51, n. 8, p. 85-86, Aug. 1972.
Lackner, Higher Octanes, Less Benzene, Hydrocarbon Processs. (ISSN 0018-8190) V67 n. 10 Sect 1 67-68 (Oct. 1988), v 67, n. 10, Oct. 1988.
Gentry et.al., The petrochemistry of paraxylene, Hydrocarbon Engineering, v 19, n. 9, p. 103-109, 2014.
Yan, Effective routes enhancing p-xylene production, Petroleum Refinery Engineering, v 30, n. 12, p. 6-10, Dec. 25, 2000.
Search Report and Written Opinion for corresponding PCT application No. PCT/US2018/055402, dated Jan. 17, 2019.

\* cited by examiner

PROCESS FOR MINIMIZING BENZENE, TOLUENE, AND A RECYCLE LOOP IN A ZERO BENZENE AROMATICS COMPLEX

FIELD

The present invention relates to minimizing benzene, toluene, and an A9/A10 recycle loop in a zero benzene aromatics complex. More specifically, the present invention relates to minimizing benzene, toluene, and an A9/A10 recycle loop in a zero benzene aromatics complex wherein the aromatic feed has a low methyl to phenyl ratio, and where the aromatic feed has a high methyl to phenyl ratio.

BACKGROUND

Zero-benzene aromatics complexes are attractive to purified terephthalic acid producers because more of the feedstock is converted to the desired product (para-xylene) as opposed to a side product (benzene). Toluene methylation technology enables zero-benzene aromatics complexes. The current flow scheme converts all the toluene in a toluene methylation unit, and all the benzene and A9/A10 aromatics in a trans-alkylation unit. In the current flow scheme, the trans-alkylation unit converts benzene and A9/A10 aromatics to a trans-alkylation product comprising benzene through A11+ aromatics with toluene and xylenes as the focus. The problem with the current flow scheme is that some feed cases require very large recycle loops through fractionation columns in order to convert the benzene and A9/A10 aromatics to extinction. These recycle loops require high costs. This is particularly the case when there is extra benzene in the feed (e.g., an aromatics complex with an external benzene feed or integrated with benzene producing technologies such as reforming or dehydrocyclodimerization) or when there is extra A9/A10 material in the feed or produced in one of the aromatics complex units (e.g., toluene methylation).

In one embodiment, the disclosure addresses a case where extra benzene and toluene are produced or brought into the existing aromatics complex. The stoichiometry of benzene and toluene relative to A9+ in the feed is significantly below methyl to phenyl ratio of 1.5 in the current flow scheme. This leads to low per-pass conversion of benzene in the trans-alkylation unit, resulting in very high benzene recycle. This situation would call for more efficient and balanced methylation vs. trans-alkylation unit operations to minimize the benzene and toluene recycle. In this disclosure, at least a portion of the benzene is diverted from the trans-alkylation unit and sent to the toluene methylation unit. Benzene reactivity is shown to be at least half of the toluene reactivity in a toluene methylation unit.

In another embodiment, the disclosure addresses a case where extra A9+ materials are produced or brought into the existing aromatics complex. The stoichiometry of benzene and toluene relative to A9+ is significantly above methyl to phenyl ratio of 1.5 in the current flow scheme. This leads to low per-pass conversion of A9+ in the trans-alkylation unit, resulting in very high A9+ recycle. This situation would call for more efficient and balanced methylation vs. trans-alkylation unit operations to minimize the A9+ recycle. In this disclosure, at least a portion of the toluene is diverted from the toluene methylation unit and sent to the trans-alkylation unit. The trans-alkylation unit converts benzene, toluene, and A9/A10 aromatics at high per-pass conversion to a trans-alkylation product comprising benzene through A11+ aromatics with toluene and xylenes as the focus.

SUMMARY

A first embodiment of the invention comprises a process for producing no benzene in an aromatics complex, comprising passing an aromatics stream having a high methyl to phenyl ratio to a benzene column to produce a benzene column overhead stream and a benzene column bottoms stream; passing the benzene column overhead stream to a trans-alkylation unit of A9+ with benzene to produce a trans-alkylation product stream and passing the benzene column bottoms stream to a toluene column which produces a toluene column overhead stream and a toluene column bottoms stream; passing a first portion of the toluene column overhead stream to the trans-alkylation unit of A9+ with toluene and a second portion of the toluene column overhead stream to a toluene methylation unit to produce a toluene methylation unit product stream; and passing the toluene column bottoms stream to a fractionation zone to produce an overhead stream, a bottoms stream, and a middle boiling fraction, wherein the middle boiling fraction is sent to the trans-alkylation unit of A9+ with benzene and toluene.

A second embodiment of the invention is a process for producing no benzene in an aromatics complex, comprising passing an aromatics stream having a methyl to phenyl ratio above 1.5 to a benzene column to produce a benzene column overhead stream and a benzene column bottoms stream; passing the benzene column overhead stream to a trans-alkylation unit of A9+ with benzene to produce a trans-alkylation product stream and passing the benzene column bottoms stream to a toluene column which produces a toluene column overhead stream and a toluene column bottoms stream; passing a first portion of the toluene column overhead stream to the trans-alkylation unit of A9+ with toluene and a second portion of the toluene column overhead stream to a toluene methylation unit to produce a toluene methylation unit product stream; and passing the toluene column bottoms stream to a fractionation zone to produce an overhead stream, a bottoms stream, and a middle boiling fraction, wherein the middle boiling fraction is sent to the trans-alkylation unit of A9+ with benzene and toluene.

In the foregoing, all temperatures are set forth in degrees Celsius and, all parts and percentages are by weight, unless otherwise indicated. Other objects, advantages and applications of the present invention will become apparent to those skilled in the art from the following detailed description and drawings. Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

DEFINITIONS

Figure 1:
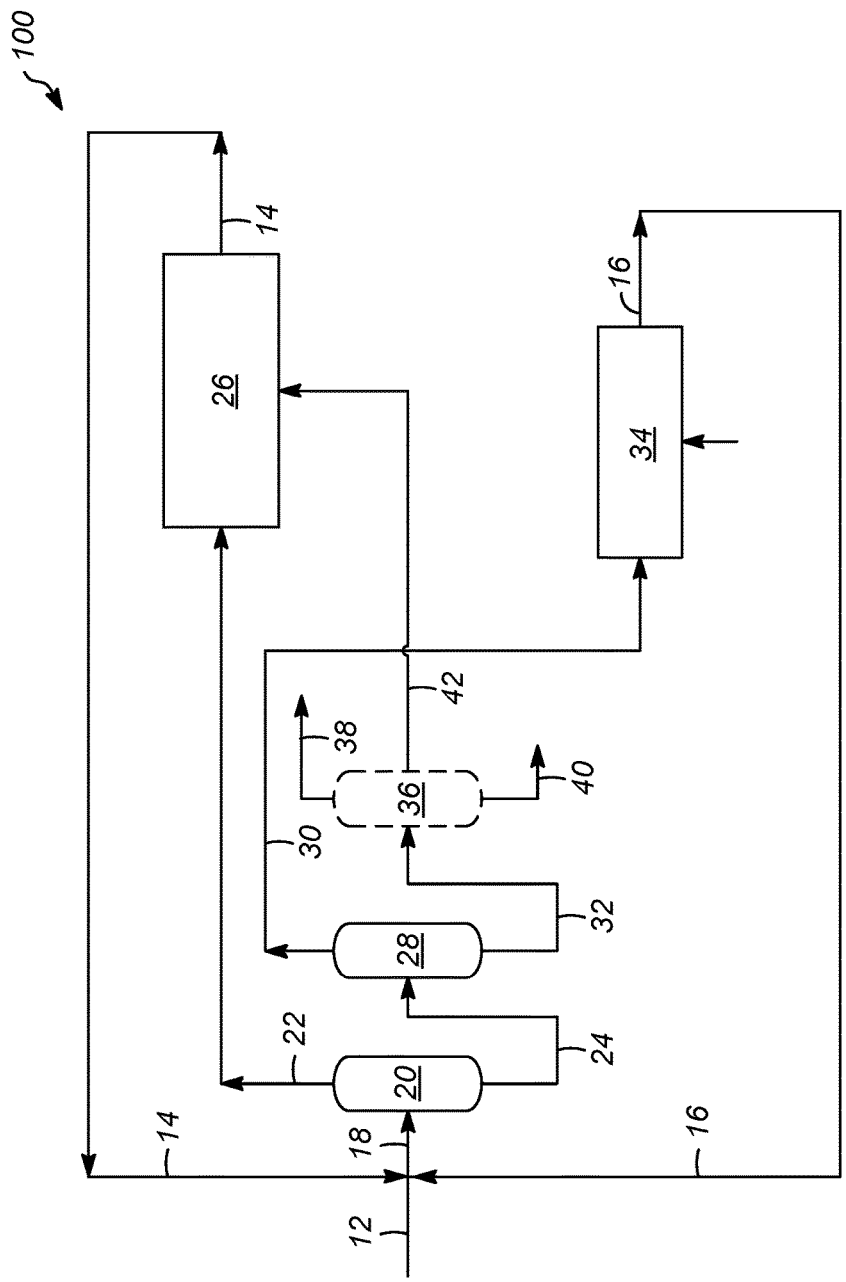
FIG. 1 illustrates the current design of the zero-benzene aromatics process.

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As depicted, process flow lines in the drawings can be referred to interchangeably as, e.g., lines, pipes, feeds, gases, products, discharges, parts, portions, or streams.

The term "passing" means that the material passes from a conduit or vessel to an object.

As used herein, the term "toluene methylation" may also be used for benzene methylation.

As used herein, the term "methyl to phenyl ratio" can be calculated as follows:

$$\text{Methyl:Phenyl Mole Ratio} = [\text{Total number of methyls}]/[\text{Total Aromatic Rings}]$$

Where: Total Aromatic Rings=sum over all i (MS(i)/MW(i)*NR(i))
 Total Number of Methyls=sum over all i (MS(i)/MW(i)*ME(i))
 i: Compound Species
 Molecular weight for species i: MW(i)
 Number of aromatic (phenyl) rings for species i: NR(i)
 Number of methyl groups attached onto the phenyl rings of species i: ME(i)
 The mass content of species i, in the feed: MS(i)

Exemplary calculations for various compound species are depicted below:

Single ring aromatics: i: Toluene, NR(i)=1, ME(i)=1; i: Xylene, NR(i)=1, ME(i)=2

Fused aromatic rings: i: Indane, NR(i)=1, ME(i)=0; is Tetralin, NR(i)=1, ME(i)=0;

i: Naphthalene, NR(i)=2, ME(i)=0

Substituents on saturated fused ring: i: 1-methyl-indane and 2-methyl-indane (where one methyl group is attached to the five carbon ring), NR(i)=1, ME(i)=0

Substituents on unsaturated fused ring: i: 4-methyl-indane and 5-methyl-indane (where one methyl group is attached to the phenyl ring), NR(i)=1, ME(i)=1; i: dimethyl 2,6-naphthalene, NR(i)=2, ME(i)=2

Hence, methyl groups are counted when attached to an aromatic group, e.g., phenyl, and not counted when attached to a full or partial, e.g., fused, saturated ring for fused-ring compounds having aromatic and saturated rings.

DETAILED DESCRIPTION

The following detailed description is merely exemplary in nature and is not intended to limit the application and uses of the embodiment described. Furthermore, there is no intention to be bound by any theory presented in the preceding background or the following detailed description.

Figure 2:
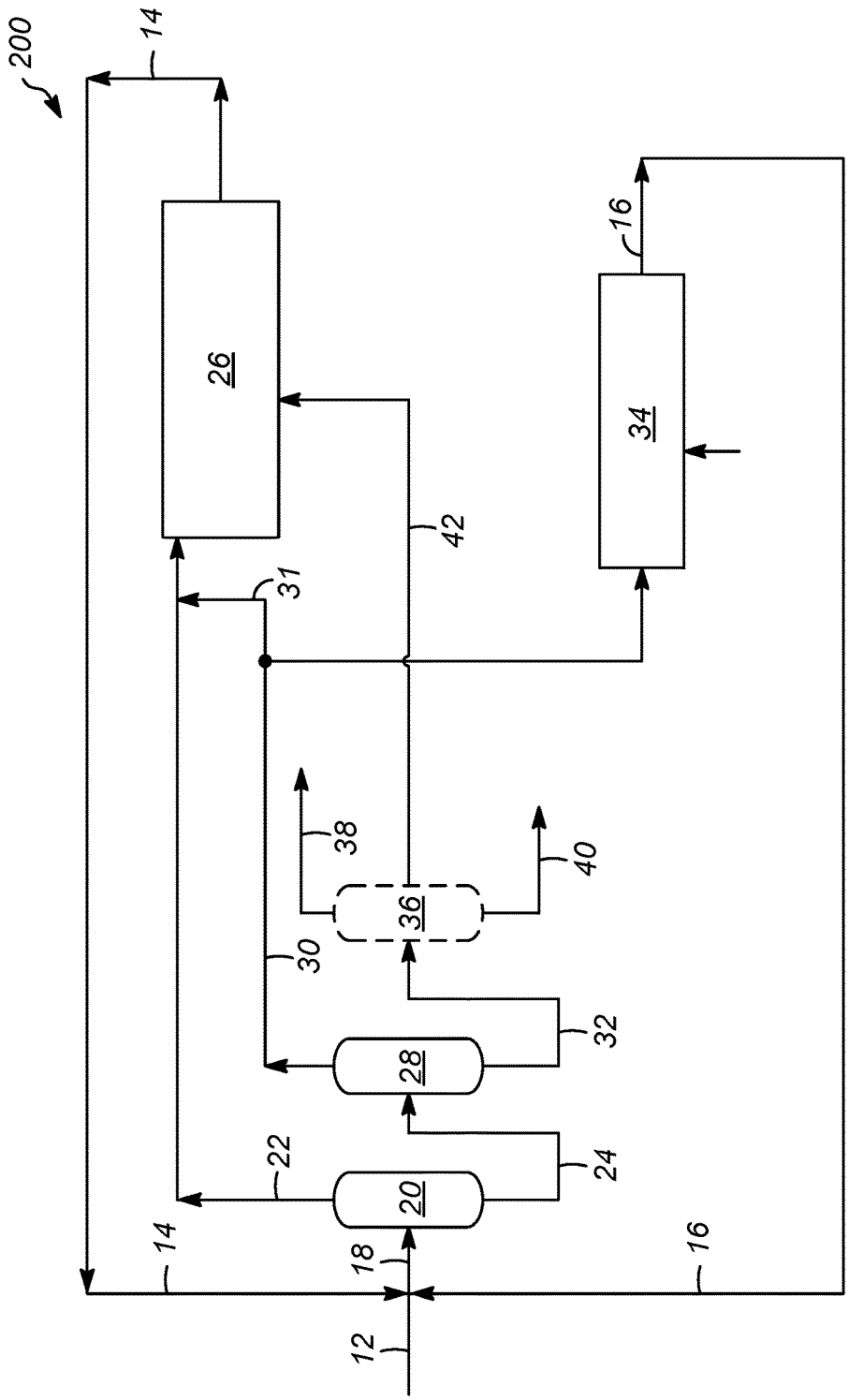
FIG. 2 illustrates the high methyl to phenyl ratio zero-benzene aromatics process.
Figure 3:
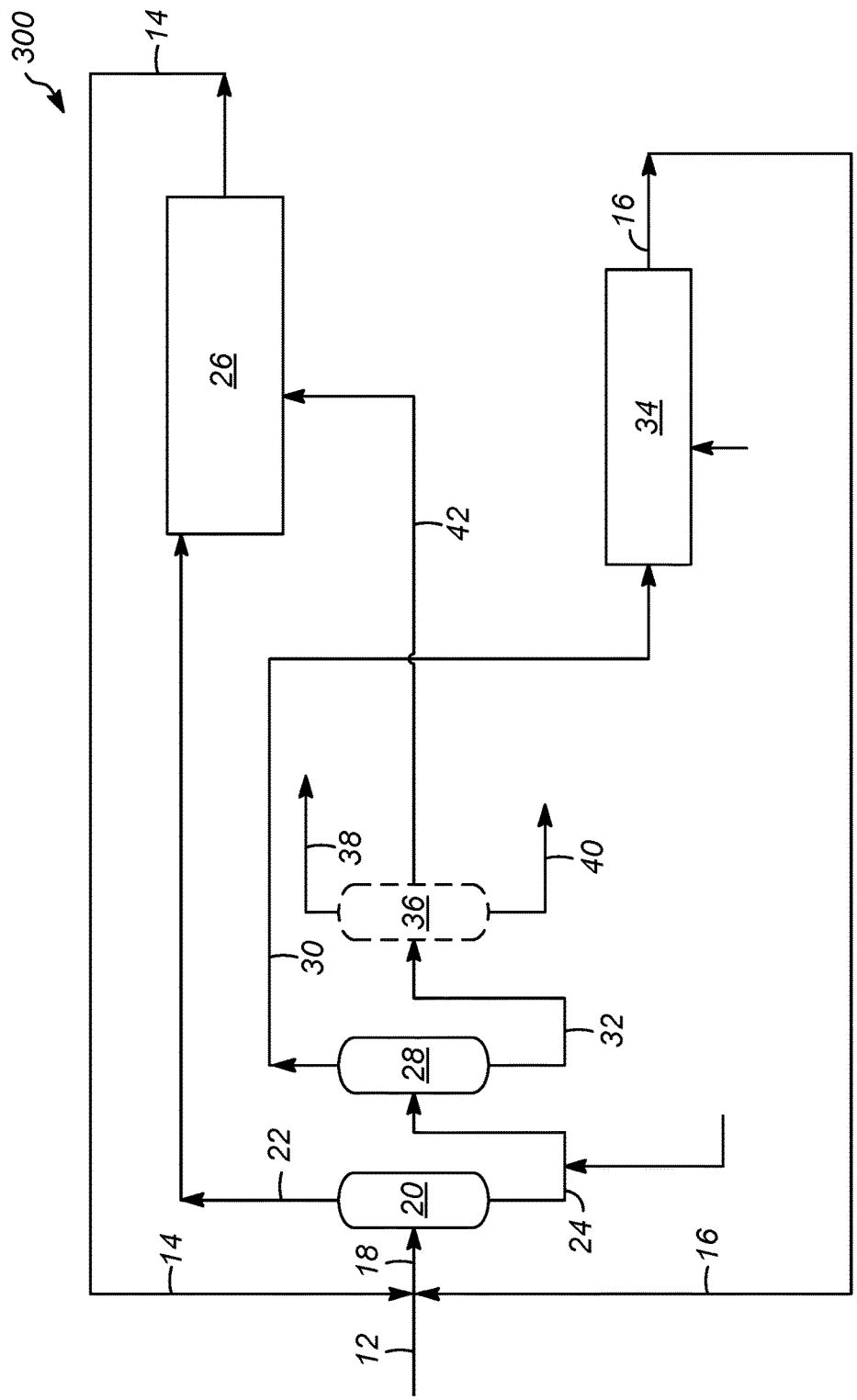
FIG. 3 illustrates the low methyl to phenyl ratio zero-benzene aromatics process.

The description of the apparatus of this invention is presented with reference to the drawings. FIGS. 2 and 3 are simplified diagrams of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to a zero-benzene aromatics process. As shown in FIG. 1, the current design of the process 100 for producing no benzene in an aromatics complex. In FIG. 1, the aromatic feed 12 is combined with stream 14 and stream 16 to produce stream 18 which is sent to a benzene column 20. The overhead stream 22 comprising benzene is sent to a trans-alkylation unit 26 and the bottoms stream 24 is sent to a toluene column. The toluene column overhead stream 30 comprising toluene is sent to a toluene methylation unit 34 and the toluene column bottoms stream 32 is sent to another fractionation zone 36. The overhead stream from the fractionation zone comprises mixed xylenes and the bottoms stream 40 comprises heavy aromatics. A stream 42 comprising A9-A10 is sent to the trans-alkylation unit 26. The product stream 14 from the trans-alkylation unit 26 is sent back to be combined with the aromatic feed 12. The product stream from the toluene methylation unit 34 is also sent back to be combined with the aromatic feed 12.

In the example shown in FIG. 2, the aromatic feed 12 has a high methyl to phenyl ratio. As shown in FIG. 2, the new design of the process 200 for producing no benzene in an aromatics complex. In FIG. 2, the aromatic feed having a high methyl to phenyl ratio 12 is combined with stream 14 and stream 16 to produce stream 18 which is sent to a benzene column 20. The methyl to phenyl ratio of stream 12 may be above about 1.5. The overhead stream 22 comprising benzene is sent to a trans-alkylation unit 26 and the bottoms stream 24 is sent to a toluene column. The toluene column overhead stream 30 comprising toluene is sent to a toluene methylation unit 34 and the toluene column bottoms stream 32 is sent to another fractionation zone 36. Here, there is an addition stream 31 comprising toluene that is cut from stream 30 and sent to be combined with stream 22 which is being sent to the trans-alkylation unit 26. The overhead stream from the fractionation zone comprises mixed xylenes and the bottoms stream 40 comprises heavy aromatics. Stream 42 comprising A9-A10 is sent to the trans-alkylation unit 26. The product stream 14 from the trans-alkylation unit 26 is sent back to be combined with the aromatic feed 12. The product stream from the toluene methylation unit 34 is also sent back to be combined with the aromatic feed 12.

In the example shown in FIG. 3, the aromatic feed 12 has a low methyl to phenyl ratio. As shown in FIG. 3, the new design of the process 300 for producing no benzene in an aromatics complex. In FIG. 3, the aromatic feed having a low methyl to phenyl ratio 12 is combined with stream 14 and stream 16 to produce stream 18 which is sent to a benzene column 20. Here, there is more benzene sent to the bottoms stream 24. The process conditions of the benzene column 20 are configured so that more benzene is allowed in the benzene column bottoms. The methyl to phenyl ratio of stream 12 may be between about 0 and about 1.5. The overhead stream 22 comprising benzene is sent to a trans-alkylation unit 26 and the bottoms stream 24 is sent to a toluene column. The toluene column overhead stream 30 comprising toluene and benzene is sent to a toluene methylation unit 34 and the toluene column bottoms stream 32 is sent to another fractionation zone 36. The overhead stream from the fractionation zone comprises mixed xylenes and the bottoms stream 40 comprises heavy aromatics. Stream 42 comprising A9-A10 is sent to the trans-alkylation unit 26. The product stream 14 from the trans-alkylation unit 26 is sent back to be combined with the aromatic feed 12. The product stream from the toluene methylation unit 34 is also sent back to be combined with the aromatic feed 12.

While the invention has been described with what are presently considered the preferred embodiments, it is to be understood that the invention is not limited to the disclosed embodiments, but it is intended to cover various modifications and equivalent arrangements included within the scope of the appended claims.

EXAMPLES

The following examples listed in Table 1 are intended to further illustrate the subject embodiments. These illustrations of different embodiments are not meant to limit the claims to the particular details of these examples.

TABLE 1

| Catalyst: 65/35 MWW(SAR~47)/Al2O3 | | Feed | Product | |
|---|---|---|---|---|
| Conditions | WHSV, hr−1 | 1.9 | 1.9 | 3.8 |
| | Catalyst max temperature, C. | 287 | 291 | 289 |

TABLE 1-continued

| Catalyst: 65/35 MWW(SAR~47)/Al2O3 | | Feed | Product | |
|---|---|---|---|---|
| | Pressure, psig | 48 | 295 | 292 |
| Yield, wt % | C1-C4 | 0.00 | 0.19 | 1.07 | 0.92 |
| | Benzene | 70.54 | 39.40 | 49.24 | 61.17 |
| | Toluene | 28.03 | 37.27 | 33.20 | 29.35 |
| | A8 | 0.29 | 12.23 | 8.92 | 4.58 |
| | A9 (excluding indane) | 0.12 | 5.03 | 2.92 | 1.23 |
| | A10 (excluding methylindanes) | 0.03 | 1.79 | 1.12 | 0.43 |
| | A11+ (single ring) | 0.06 | 3.54 | 3.47 | 2.28 |
| | Other | 0.95 | 1.84 | 1.50 | 1.04 |
| Aromatics conversion, mol % | Benzene | | 38.1 | 24.5 | 9.9 |
| | Toluene | | 64.7 | 43.2 | 20.0 |
| Methanol conversion, wt % | | | 94 | 62 | 32 |
| Benzene reactivity, % of Toluene | | | 59 | 57 | 49 |
| | pX/X | | 45.6 | 48.2 | 44.5 |
| | oX/X | | 30.8 | 37.0 | 41.2 |
| | mX/X | | 23.6 | 14.8 | 14.2 |

Table 1 demonstrates that benzene can be converted at high per pass conversion in a toluene methylation unit. Non-aromatics are excluded because they don't react with methanol at conditions used. Oxygenates (methanol and dimethyl ether) are also excluded, and some components are grouped together. Benzene conversion is defined as decrease of benzene in product relative to feed (in moles), and toluene conversion is defined as a sum of A8-A12 in product relative to toluene in feed (also in moles). Methanol conversion estimated by counting alkyl groups in aromatics. Benzene "reactivity" is a simple ratio of benzene to toluene conversion, in %. Generally, benzene reactivity is shown to be at least half of the toluene reactivity in a toluene methylation unit. It is further noted that contents of para-xylene in xylene fractions exceeds the equilibrium concentration of about 24%. It should be noted that various changes and modifications to the presently preferred embodiments described herein will be apparent to those skilled in the art. Such changes and modifications may be made without departing from the spirit and scope of the present subject matter and without diminishing its attendant advantages.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing no benzene in an aromatics complex, comprising passing an aromatics stream having a high methyl to phenyl ratio to a benzene column to produce a benzene column overhead stream and a benzene column bottoms stream; passing the benzene column overhead stream to a trans-alkylation unit of A9+ with benzene to produce a trans-alkylation product stream and passing the benzene column bottoms stream to a toluene column which produces a toluene column overhead stream and a toluene column bottoms stream; passing a first portion of the toluene column overhead stream to the trans-alkylation unit of A9+ with toluene and a second portion of the toluene column overhead stream to a toluene methylation unit to produce a toluene methylation unit product stream; and passing the toluene column bottoms stream to a fractionation zone to produce an overhead stream, a bottoms stream, and a middle boiling fraction, wherein the middle boiling fraction is sent to the trans-alkylation unit of A9+ with benzene and toluene. An embodiment of the invention is one, any or all of prior embodiments in this paragraph up through the first embodiment in this paragraph, wherein the toluene methylation unit produces an effluent containing xylenes with para-xylene selectivity between 20% and 99.9% within the xylene fraction. An embodiment of the invention is one, any or all of prior embodiments in this paragraph up through the first embodiment in this paragraph, wherein the toluene methylation unit produces an effluent containing xylenes with para-xylene selectivity preferably between 50% and 99.9% within the xylene fraction. An embodiment of the invention is one, any or all of prior embodiments in this paragraph up through the first embodiment in this paragraph, wherein the methyl to phenyl ratio of the aromatic steam is above 1.0. An embodiment of the invention is one, any or all of prior embodiments in this paragraph up through the first embodiment in this paragraph, wherein the methyl to phenyl ratio of the aromatic stream is above 1.5. An embodiment of the invention is one, any or all of prior embodiments in this paragraph up through the first embodiment in this paragraph, wherein the methyl to phenyl ratio of the aromatic stream is above 1.8. An embodiment of the invention is one, any or all of prior embodiments in this paragraph up through the first embodiment in this paragraph, wherein the fractionation zone comprises a plurality of fractionation units. An embodiment of the invention is one, any or all of prior embodiments in this paragraph up through the first embodiment in this paragraph, wherein a portion of the toluene column overhead stream is sent directly to the trans-alkylation unit. An embodiment of the invention is one, any or all of prior embodiments in this paragraph up through the first embodiment in this paragraph, wherein a portion of the toluene column overhead stream is combined with the benzene column overhead stream before being sent to the trans-alkylation unit. An embodiment of the invention is one, any or all of prior embodiments in this paragraph up through the first embodiment in this paragraph, further comprising passing methanol or another alkylation agent to the toluene methylation unit. An embodiment of the invention is one, any or all of prior embodiments in this paragraph up through the first embodiment in this paragraph, further comprising sending a portion of the toluene column overhead to the benzene column overhead stream. An embodiment of the invention is one, any or all of prior embodiments in this paragraph up through the first embodiment in this paragraph, wherein toluene is allowed to pass to the overhead of the benzene column. An embodiment of the invention is one, any or all of prior embodiments in this paragraph up through the first embodiment in this paragraph, wherein the toluene methylation unit produces some product with methyl to phenyl ratio above 2.

A second embodiment of the invention is a process for producing no benzene in an aromatics complex, comprising passing an aromatics stream having a methyl to phenyl ratio above 1.5 to a benzene column to produce a benzene column overhead stream and a benzene column bottoms stream; passing the benzene column overhead stream to a trans-alkylation unit of A9+ with benzene to produce a trans-alkylation product stream and passing the benzene column bottoms stream to a toluene column which produces a toluene column overhead stream and a toluene column bottoms stream; passing a first portion of the toluene column overhead stream to the trans-alkylation unit of A9+ with toluene and a second portion of the toluene column overhead stream to a toluene methylation unit to produce a toluene methylation unit product stream; and passing the toluene column bottoms stream to a fractionation zone to produce an overhead stream, a bottoms stream, and a middle boiling fraction, wherein the middle boiling fraction is sent to the trans-alkylation unit of A9+ with benzene and toluene. An embodiment of the invention is one, any or all of prior embodiments in this paragraph up through the second embodiment in this paragraph, wherein the fractionation zone comprises a plurality of fractionation units. An embodiment of the invention is one, any or all of prior embodiments in this paragraph up through the second embodiment in this paragraph, wherein the toluene methylation unit produces an effluent containing xylenes with para-xylene selectivity between 20% and 99.9% within the xylene fraction. An embodiment of the invention is one, any or all of prior embodiments in this paragraph up through the second embodiment in this paragraph, wherein the toluene methylation unit produces an effluent containing xylenes with para-xylene selectivity preferably between 50% and 99.9% within the xylene fraction. An embodiment of the invention is one, any or all of prior embodiments in this paragraph up through the second embodiment in this paragraph, wherein the portion of the toluene column overhead stream is sent directly to the trans-alkylation unit. An embodiment of the invention is one, any or all of prior embodiments in this paragraph up through the second embodiment in this paragraph, wherein the portion of the toluene column overhead stream is combined with the benzene column overhead stream before being sent to the trans-alkylation unit. An embodiment of the invention is one, any or all of prior embodiments in this paragraph up through the second embodiment in this paragraph, wherein the toluene methylation unit produces some product with methyl to phenyl ratio above 2.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for reducing benzene in an aromatics complex, comprising:
    passing an aromatics stream having a methyl to phenyl ratio above 1.0 to a benzene column to produce a benzene column overhead stream comprising benzene and a benzene column bottoms stream comprising toluene and aromatics having 9+ carbons;
    passing the benzene column overhead stream to a trans-alkylation unit and transalkylating aromatics having 9+ carbons with benzene to produce a benzene trans-alkylation product stream;
    passing the benzene column bottoms stream to a toluene column to produce a toluene column overhead stream comprising toluene and a toluene column bottoms stream comprising aromatics having 9+ carbon;
    passing a first portion of the toluene column overhead stream to the trans-alkylation unit and transalkylating aromatics having 9+ carbons with toluene to produce a toluene transalkylation product stream;

passing a second portion of the toluene column overhead stream to a toluene methylation unit to produce a toluene methylation unit product stream containing xylenes with para-xylene selectivity between 20% and 99.9% within the xylenes;

passing the toluene column bottoms stream to a fractionation zone to produce an overhead stream comprising xylenes, a bottoms stream comprising heavy aromatics, and a middle boiling fraction comprising aromatics having 9-10 carbons;

passing the middle boiling fraction from the fractionation zone to the trans-alkylation unit;

recycling the benzene trans-alkylation product stream to the benzene column; and, recycling the toluene methylation unit product stream to the benzene column.

2. The process of claim 1, wherein the toluene methylation unit produces an effluent containing xylenes with para-xylene selectivity between 50% and 99.9% within the xylene fraction.

3. The process of claim 1, wherein the methyl to phenyl ratio of the aromatic stream is above 1.5.

4. The process of claim 1, wherein the methyl to phenyl ratio of the aromatic stream is above 1.8.

5. The process of claim 1, wherein the fractionation zone comprises a plurality of fractionation units.

6. The process of claim 1, wherein a portion of the toluene column overhead stream is sent directly to the trans-alkylation unit.

7. The process of claim 1, wherein a portion of the toluene column overhead stream is combined with the benzene column overhead stream before being sent to the trans-alkylation unit.

8. The process of claim 1, further comprising passing methanol or another alkylation agent to the toluene methylation unit.

9. The process of claim 1, further comprising sending a portion of the toluene column overhead to the benzene column overhead stream.

10. The process of claim 1, wherein toluene is allowed to pass to the overhead of the benzene column.

11. The process of claim 1, wherein the toluene methylation unit produces some product with methyl to phenyl ratio above 2.

12. A process for reducing benzene in an aromatics complex, comprising:

passing an aromatics stream having a methyl to phenyl ratio above 1.5 to a benzene column to produce a benzene column overhead stream comprising benzene and a benzene column bottoms stream comprising toluene and aromatics having 9+ carbons;

passing the benzene column overhead stream to a trans-alkylation unit;

passing the benzene column bottoms stream to a toluene column to produce a toluene column overhead stream comprising toluene and a toluene column bottoms stream comprising aromatics having 9+ carbon;

passing a first portion of the toluene column overhead stream to the trans-alkylation unit;

transalkylating aromatics having 9+ carbons with toluene from the first portion of the toluene column overhead stream and with benzene from the benzene column overhead stream to produce a transalkylation product stream;

passing a second portion of the toluene column overhead stream to a toluene methylation unit to produce a toluene methylation unit product stream;

passing the toluene column bottoms stream to a fractionation zone to produce an overhead stream comprising xylenes, a bottoms stream comprising heavy aromatics, and a middle boiling fraction comprising aromatics having 9-10 carbons;

passing the middle boiling fraction from the fractionation zone to the trans-alkylation unit;

recycling the benzene trans-alkylation product stream to the benzene column; and, recycling the toluene methylation unit product stream to the benzene column.

13. The process of claim 12, wherein the fractionation zone comprises a plurality of fractionation units.

14. The process of claim 12, wherein the toluene methylation unit produces an effluent containing xylenes with para-xylene selectivity between 20% and 99.9% within the xylenes.

15. The process of claim 12, wherein the toluene methylation unit produces an effluent containing xylenes with para-xylene selectivity between 50% and 99.9% within the xylenes.

16. The process of claim 12, wherein the portion of the toluene column overhead stream is sent directly to the trans-alkylation unit.

17. The process of claim 12, wherein the portion of the toluene column overhead stream is combined with the benzene column overhead stream before being sent to the trans-alkylation unit.

18. The process of claim 12, wherein the toluene methylation unit produces some product with methyl to phenyl ratio above 2.

* * * * *